US012708694B2

(12) United States Patent
Slotkin et al.

(10) Patent No.: US 12,708,694 B2
(45) Date of Patent: Aug. 18, 2026

(54) PROACTIVE AIR/SURFACE DECONTAMINATION SYSTEM AND DEVICES FOR PORTABLE ROOM SIZED HYDROXYL GENERATORS

(71) Applicant: Radical Clean Solutions Ltd., Long Beach, NY (US)

(72) Inventors: Roger Slotkin, Long Beach, NY (US); Ralph T. Kubitzki, Plantation, FL (US)

(73) Assignee: Radical Clean Solutions Ltd., Long Beach, NY (US)

( * ) Notice: Subject to any disclaimer, the term of this patent is extended or adjusted under 35 U.S.C. 154(b) by 676 days.

(21) Appl. No.: 18/076,176

(22) Filed: Dec. 6, 2022

(65) Prior Publication Data

US 2023/0173132 A1 Jun. 8, 2023

Related U.S. Application Data

(63) Continuation-in-part of application No. 17/861,181, filed on Jul. 9, 2022, now Pat. No. 12,594,356, and a (Continued)

(51) Int. Cl.
*A61L 9/20* (2006.01)
*A61L 2/10* (2006.01)

(52) U.S. Cl.
CPC . *A61L 9/20* (2013.01); *A61L 2/10* (2013.01); *A61L 2209/111* (2013.01); *A61L 2209/14* (2013.01)

(58) Field of Classification Search
CPC ........ A61L 2/10; A61L 9/20; A61L 2209/111; A61L 2209/12; A61L 2209/15; A61L 2209/20
See application file for complete search history.

(56) References Cited

U.S. PATENT DOCUMENTS 2,945,554 A 7/1960 Berly
5,968,455 A * 10/1999 Brickley .................. A61L 9/20 362/267

(Continued)

FOREIGN PATENT DOCUMENTS

JP 2010080195 A 4/2010
WO PCT/US2022/051886 A 5/2023

OTHER PUBLICATIONS

LSE (Light Spectrum Enterprises); "Shop UV Lighting-GPH457T5L/4P Ultraviolet UV Lamp Bulb 4-pin Base 18" GPH457T5"; 1300 Industrial Blvd.-Ste B3, Southampton, PA 18966.

(Continued)

*Primary Examiner* — Timothy C Cleveland
(74) *Attorney, Agent, or Firm* — Alfred M. Walker; Thomas A. O'Rourke; James Bongiorno

(57) ABSTRACT

A portable air purifier includes: a housing, partition wall, a baffle, air blower, and hydroxyl generator. The housing has an air inlet and air outlet. The partition wall extends downwardly from a top wall forming first and second vertical chambers. The baffle extends from a first side wall to the partition wall separating the first vertical chamber into upper and lower chambers. The partition wall extends partway to a housing bottom wall providing an interconnection between the lower chamber and second vertical chamber. The blower positioned in the lower chamber creates a pressurize air flow. A particulate filter is positioned between the air inlet and the blower. The hydroxyl generator is positioned in the second vertical chamber and includes a UV bulb. An opening in the partition wall proximate to the top wall permits purified air from the hydroxyl generator to exit through the air outlet.

7 Claims, 12 Drawing Sheets

Related U.S. Application Data continuation-in-part of application No. 17/826,555, filed on May 27, 2022, now abandoned, and a continuation-in-part of application No. 17/713,959, filed on Apr. 5, 2022, now Pat. No. 12,246,116, which is a continuation-in-part of application No. 17/674,763, filed on Feb. 17, 2022, now Pat. No. 12,390,547, said application No. 17/826,555 is a continuation-in-part of application No. 17/590,270, filed on Feb. 1, 2022, now abandoned, which is a continuation-in-part of application No. 17/545,919, filed on Dec. 8, 2021, said application No. 17/861,181 is a continuation-in-part of application No. 17/545,919, filed on Dec. 8, 2021, said application No. 17/674,763 is a continuation-in-part of application No. 17/545,919, filed on Dec. 8, 2021.

(56) References Cited

U.S. PATENT DOCUMENTS

| | | | | |
|---|---|---|---|---|
| 6,497,840 | B1 | 12/2002 | Palestro et al. | |
| 6,613,277 | B1 | 9/2003 | Monagan | |
| 6,805,733 | B2 | 10/2004 | Engel et al. | |
| 7,416,588 | B2 * | 8/2008 | Burrows | A61L 9/20 422/24 |
| 7,837,933 | B2 | 11/2010 | Sevack et al. | |
| 7,976,195 | B2 | 7/2011 | Engel et al. | |
| 7,988,923 | B2 | 8/2011 | Fink et al. | |
| 8,252,099 | B2 | 8/2012 | Worrilow | |
| 8,252,100 | B2 | 8/2012 | Worrilow | |
| 8,545,753 | B2 | 10/2013 | Sevack et al. | |
| 8,747,753 | B2 | 6/2014 | Engel et al. | |
| 9,168,323 | B2 | 10/2015 | Morneault | |
| 9,522,210 | B2 | 12/2016 | Worrilow | |
| 9,675,725 | B2 | 6/2017 | Worrilow | |
| 9,884,135 | B2 | 2/2018 | Bystrzynski et al. | |
| 9,956,306 | B2 | 5/2018 | Brais et al. | |
| 9,980,748 | B2 | 5/2018 | Worrilow | |
| 10,857,249 | B2 | 12/2020 | Brais et al. | |
| 11,103,611 | B2 | 8/2021 | Elde et al. | |
| 2008/0073565 | A1 | 3/2008 | Jeon | |
| 2015/0114822 | A1 | 4/2015 | Greco | |
| 2017/0225973 | A1 | 8/2017 | Henderson et al. | |
| 2020/0084983 | A1 | 3/2020 | Liang et al. | |
| 2020/0129972 | A1 | 4/2020 | Ozaki et al. | |
| 2021/0339184 | A1 * | 11/2021 | Hourani | F24F 8/10 |

OTHER PUBLICATIONS

Hao Chen, et al.; "A Hydroxyl radical detection system using gas expansion and fast gating laser-induced fluorescence techniques"; The Research Center for Eco-Environmental Sciences, Chinese Academy of Sciences; Journal of Environmental Sciences 65 (2018) 190-200; published by Elsevier B.V.; http//dx.doi.org/10.1016/i.jes.2017.03.012.

* cited by examiner

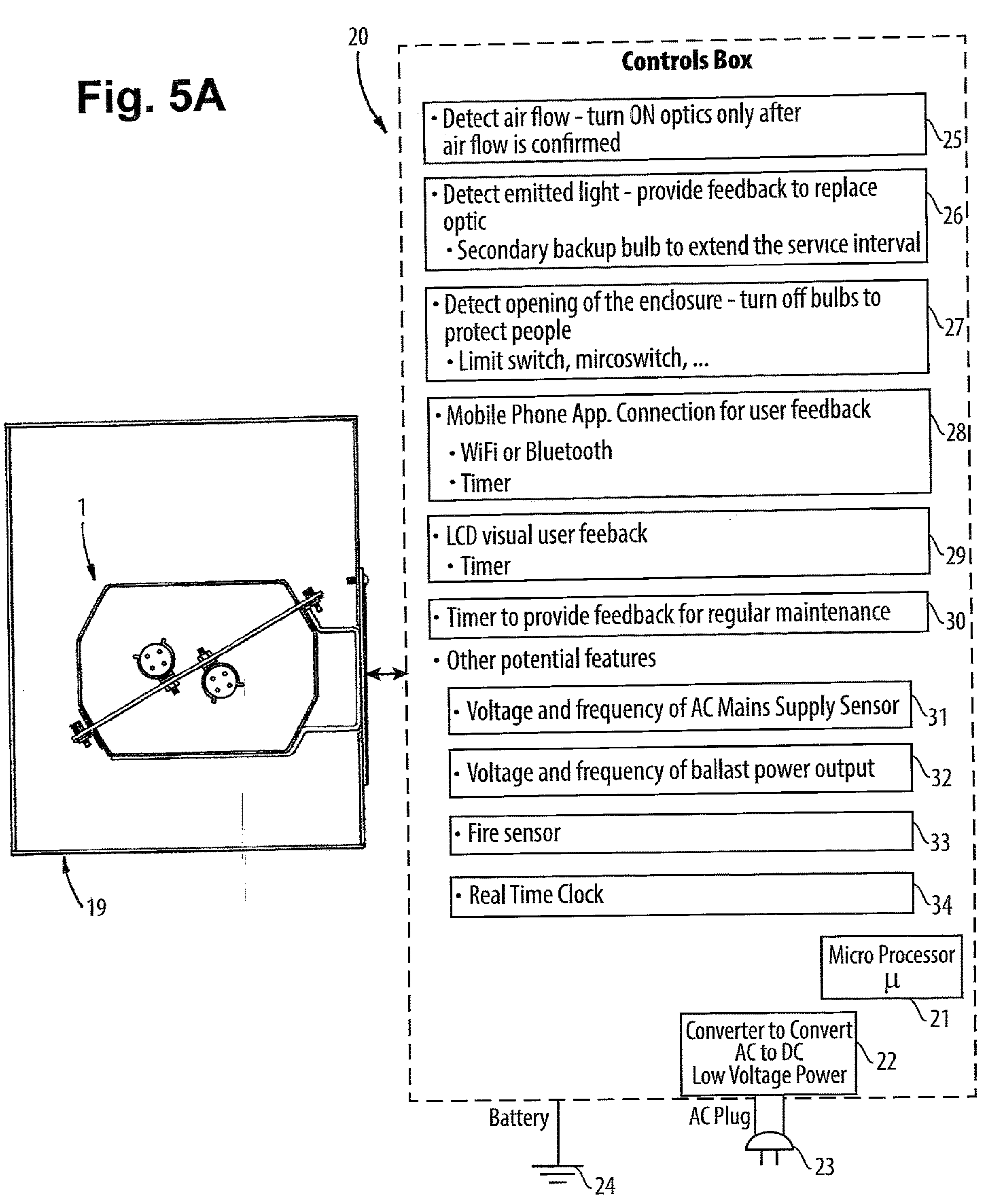
Fig. 5A
20
Controls Box
• Detect air flow - turn ON optics only after air flow is confirmed
25
• Detect emitted light - provide feedback to replace optic
• Secondary backup bulb to extend the service interval
26
• Detect opening of the enclosure - turn off bulbs to protect people
• Limit switch, mircoswitch, ...
27
• Mobile Phone App. Connection for user feedback
• WiFi or Bluetooth
• Timer
28
• LCD visual user feeback
• Timer
29
• Timer to provide feedback for regular maintenance
30
• Other potential features
• Voltage and frequency of AC Mains Supply Sensor
31
• Voltage and frequency of ballast power output
32
• Fire sensor
33
• Real Time Clock
34
Micro Processor
μ
21
Converter to Convert AC to DC Low Voltage Power
22
Battery
24
AC Plug
23
1
19

HVAC Unit Block Diagram

Consumer Unit Block Diagram

841
Air Path A
819b
801
800
820a
890a
860a
821
819c
840
820
819d
812
813
806
830
Air In
860
819e
890
851
850
845
850
819a
845a
845b
845c
851

PROACTIVE AIR/SURFACE DECONTAMINATION SYSTEM AND DEVICES FOR PORTABLE ROOM SIZED HYDROXYL GENERATORS

RELATED APPLICATIONS

This application is a continuation-in-part (CIP) of application Ser. No. 17/861,181 filed Jul. 9, 2022, which '181 application is a continuation-in-part (CIP) of application Ser. No. 17/545,919 filed Dec. 8, 2021. This application is also a continuation-in part (CIP) of application Ser. No. 17/713,959 filed Apr. 5, 2022, which '959 application is a continuation-in-part (CIP) of application Ser. No. 17/674,763 filed Feb. 17, 2022, which '763 application is a continuation-in-part (CIP) of application Ser. No. 17/545,919 filed Dec. 8, 2021. This application is also a continuation-in-part (CIP) of application Ser. No. 17/826,555 filed May 27, 2022, which '555 application is a continuation-in-part (CIP) of application Ser. No. 17/590,270, filed Feb. 1, 2022, which '270 application is a continuation-in-part (CIP) of application Ser. No. 17/545,919 filed on Dec. 8, 2021. The '919, '270, '763, '959, '555 and '181 are each incorporated by reference herein. Applicant claims priority under 35 USC § 120 from the 919, '270, '763, '959, '555 and '181 applications.

FIELD OF THE INVENTION

The present invention relates use of a harmonic biomimicry nonchemical photonic process that results in the export of desired atmospheric hydroxyls at precisely the same rate as nature provides (2.6 million per cubic Centimeter—NASA), to neutralize toxic chemicals and pathogens in breathable air/surfaces in stationary or moving human occupied spaces.

BACKGROUND OF THE INVENTION

Ultraviolet light (UV) delivery in the form of directing ultraviolet light on unsanitary surfaces as germicides, bactericides and viricides are disadvantageous because, upon exposure to breathable air in mass transit rail and road vehicles, as well as aircraft and related airborne vehicles, such as helicopters, seating fabrics in building interior ducts and wall surfaces and other human occupied spaces, the ultraviolet light compromises fabrics and doesn't penetrate into crevices between, or in, passenger seats or flight deck seats, located in the flight deck, separately sealed away from the air of the passenger cabin, or in seating fabrics in mass transit rail and road vehicles, in building interior ducts and wall surfaces, in hydroponic greenhouses, in portable room-sized units and other human occupied spaces. Delivery of ultraviolet light for sanitation is limited because the ultraviolet light is only as effective as the actual line of sight of the ultraviolet waves.

DESCRIPTION OF THE PRIOR ART

Methods of Producing Atmospheric Hydroxyls

In the field of physics there are, to date, only a few processes in a device that generates an atmospheric hydroxyl that purportedly are useful in removing contaminants from breathable air. In theory the NASA device produces the hydroxyl in a photo catalytic oxidation (PCO) process, by emitting an ultraviolet irradiation of 254 nanometers as it interfaces with titanium dioxide ($TiO_2$) plating. In theory, the hydroxyl is produced only at the interface site of contact at the surface of the $TiO_2$. The hydroxyl does not exit the airstream and does not have any downstream interaction. Minimal air flow must be maintained at approximately 120 cfm. Typical HVAC systems utilize faster air movement at approximately 2000 cfm and this would not allow for the theoretical hydroxyl to form.

OBJECTS AND SUMMARY OF THE INVENTION

This Summary is provided to introduce a selection of concepts in a simplified form that are further described below in the Detailed Description of the Drawings. This Summary is not intended to identify key features or essential features of the claimed subject matter, nor is it intended to be used to limit the scope of the claimed subject matter.

In contrast, the present invention uses airborne hydroxyl radical molecules, which are of very small molar size and can occupy almost any given space. They can occupy dark crevices that ultraviolet line of sight cannot get access to. The present invention allows for a "Harmonic" of photonic UV frequencies to be applied within a hydroxyl producing reaction chamber. The feed stock is ambient water vapor in air which will have relative humidity, this humidity is the feed stock for the reaction chamber to produce the atmospheric hydroxyl.

This action is called "Bio-Mimicry". The present invention process is a totally green, environmentally friendly nonchemical process that results in the export of the desired atmospheric hydroxyl at precisely the same rate as nature provides, namely, at 2.6 million per cubic centimeter. The atmospheric hydroxyl process begins by exposing ambient water vapor to special UV optics having hydroxyl activation portions made of medical grade pure quartz material. The optics are designed to emit/irradiate Ultraviolet irradiation in the nanometer wavelength/Ultraviolet spectrum of between 100 and 400 nanometers, thereby producing the hydroxyls at the aforementioned quantity of 2.6 million hydroxyls per cubic centimeter, as provided in nature. This is a novel improvement over prior art NASA PCO based technology.

Hydroxyl are groups having the radical "—OH" and are represented by the symbol —OH or HO—, which can have a negative charge or be neutral. The hydroxyl functional group includes one hydrogen atom which is covalently bonded to one oxygen atom. Hydroxyl radicals are very reactive, which react quickly to hydrocarbons, carbon monoxide molecules and other air impurities, such as volatile organic compounds, (VOC), virus, bacteria and fungi.

Many closed HVAC air systems can harbor microscopic bacteria, virus (i.e., Covid-19) and fungi.

For example, aircraft and other airborne transportation vehicles, such as helicopters, seat fabrics on mass transit rail and road vehicles, in building ducts and wall surfaces, in hydroponic greenhouses, and other human occupied spaces, can harbor bacteria and virus in the separate, circulated air systems.

Also, residential rooms in dwellings or assisted living communities can harbor bacteria and virus in the separate, circulated air systems.

Therefore, the present invention is a unique and novel application method for the delivery of safe and natural hydroxyl radicals into breathable air volume containers such as agricultural hydroponic greenhouses and the agricultural plant contents therein, airline flight deck or passenger cabins, and the contents therein, seat fabrics on mass transit rail and road vehicles, in building HVAC ducts and the breathable ambient or heated or cooled air flow contents therein.

To be considered as well are upholstered chair seats, benches, contact surfaces such as grab bars, handles in building wall surfaces and other human occupied spaces.

In the present invention, the atmospheric hydroxyl radicals are generated in closed multi-sided housing, preferably polygonal, having therein two or more parallel UV optics which are multi segmented with crystal, so that when enabled, the hydroxyl radicals are generated. Hydroxyls are reactive and short lived, however the closed housing reaction chamber preferably has polygonal interior walls, so that the hydroxyl radicals will bounce against the walls so as to decontaminate within the reaction chamber as well as downstream in open air areas. Breathable air is then directed through the closed housing, so that the created and excited radicals will react quickly to air and surface impurities, such as pathogens and VOC's, rendering them neutral.

The UV optics are tubular, medical grade pure quartz. The optics are designed to emit/irradiate Ultraviolet irradiation in the nanometer wavelength/Ultraviolet spectrum of between 100 and 400 nanometers.

A multi wave 'Harmonic' is created via a multiwavelength nanometer configured optic irradiation. This configuration results in the creation of the desired atmospheric hydroxyl within the hydroxyl generator reaction chamber, which is a multi-sided reaction chamber, designed in such a way as to optimize atmospheric downstream hydroxyl production, such as for example in a polygonal-shaped housing. This multi-sided reaction chamber enables the desired atmospheric hydroxyl to be injected downstream to affect positive change. The positive change is the control/neutralization of pathogens and VOC's.

The —OH formed hydroxyl molecule is the capacitor that donates electrons to the targeted pathogen, whereupon the pathogen is therefore neutralized by the 'Electron Voltage (eV')' capacitance carried by the hydroxyl. The eV is donated at the point of contact with the pathogen.

VOC's are neutralized through the action of Bond Dissociation Energy (BDE). The capacitance of the charged hydroxyl is sufficient so as to take out of phase (decomposition) of any airborne molecular or compound structure. In Phase VOC chemistry can be harmful, therefore out-of-phase atomic airborne structures are now neutral and cannot recombine. The exception to this rule would be the recombination of water vapor, carbon dioxide and lastly oxygen ($O_2$).

This reaction sequence is essential to all life, in that water vapor feeds all life, and carbon dioxide ($CO_2$) is necessary/essential for plant life and oxygen ($O_2$) is essential for air breathers such as humans, other animals and forms of living organisms.

Because exposure of the UV light is problematic for human eyes, the interior of the reaction chamber is custom designed to arrest UV light escaping and to maximize atmospheric hydroxyl discharge. Refraction color can come out of the unit with the generated, activated hydroxyls, but never direct UV light.

Available hydrogen is low in our natural environment, so one must add electron rings to obtain optimal amplitude as opposed to adding hydrogen for increased hydroxyl production.

The polygonal shape of the reaction chamber enhances the total ability of the chamber to produce the desired atmospheric hydroxyl.

It is essential that the atmospheric hydroxyls be produced by the exposure of ambient water vapor within a confined refractive generator chamber housing to prevent diminution of the atmospheric hydroxyls. In contrast, SanUVox, by using outward facing reflectors but no confined generator chamber housing, causes a drastic diminution of the desired hydroxyl production.

In contrast the present invention, by using the polygon shaped reaction chamber, has categorically enhanced atmospheric hydroxyl production.

Because exposure of the UV light is problematic for human eyes, the interior chamber holding the reaction chamber is custom designed to arrest UV light escaping and to maximize atmospheric hydroxyl discharge. Refraction color can come out of the unit with the generated, activated hydroxyls, but never direct UV light.

Available hydrogen is low in our natural environment, so one must add electron rings to obtain optimal amplitude as opposed to adding hydrogen for increased hydroxyl production.

The polygonal shape of the reaction chamber enhances the total ability of the chamber to produce the desired atmospheric hydroxyl.

It is essential that the atmospheric hydroxyls be produced by the exposure of ambient water vapor within a confined refractive generator chamber housing to prevent diminution of the atmospheric hydroxyls. In contrast, the prior art of SanUVox, by using outward facing reflectors but no confined generator chamber housing, causes a drastic diminution of the desired hydroxyl production.

In contrast the present invention, by using the polygon shaped reaction chamber, has categorically enhanced atmospheric hydroxyl production.

However, in small environments, such as in a self-contained unit in a transit vehicle (passenger rail, passenger bus, trucking cargo shipping, etc.), or in a portable room size self-contained unit (movable with casters or wheels, or stationary mounted to a room surface, such as a wall), a fan is necessary to pull the ambient air with water vapor into the polygonal hydroxyl generator with a UV quartz optics, so that the water vapor molecules become hydroxyl radicals and thereafter are pushed by the fan out of the self-contained and/or portable unit.

For safety, an air pressure safety switch is provided, so that when air flow is not detected, this unit will be dormant. A Micro Switch shuts down all systems should the device be opened when unit is in the ON/RUN position.

Portable Room-Sized Device and System

The portable room sized unit also has a unique Internal Air Baffling System, located within an exterior housing of the portable room-sized unit, but outside of the actual polygonal clamshell hydroxyl generator, to promote the zig zag of air movement therein, to control light and prevent unwanted UV light from escaping so that the breathable air passes through the portable room sized unit. The unique device design does not allow for any UV light to exit the unit.

The portable room sized units were targeted to emulate certain characteristics required within the hospital framework. Pathogen and VOC control is of paramount concern and is inherent within the design parameters of the hydroxyl generating device. Consideration was also made with regard to sound control, wherein low air flow volume of 110 cubic feet (cf) must be quieter than 30 decibels or below (Hospital Quiet).

The portable room sized units also contain an optimal-UV light refraction tubular fan assembly, which draws in the incoming air into the hydroxyl generator chamber housing. Baffles located in the portable and duct installed hydroxyl generators allow air through the hydroxyl generator but prevent exposed UV light from escaping. The sole purpose of the baffles is to arrest any UV rays from escaping the device. Any direct line of sight to the UV source would cause a "Welders Flash" incident and may temporarily harm the eyes of the observer. This type of incident is simply not allowed and is part of the safety investigation of the validation bodies UL/CSA.

The portable room sized units also have communications capabilities, so that the Hydroxyl Generating Device can interface with a remote-control pad or mobile phone.

Safety features include a microswitch which will shut off from inadvertent opening if the reaction chamber device is "on" when it should be "off". The micro switch shuts down all systems should the device be opened when the generating unit is in operational status.

Anti-Vibration G-Force Mitigation Clips are installed, such as spring clips which operate in only one directional installation.

Reactor Rod Safety is paramount, for prevention of Reactor Rod displacement and breakage.

The portable room sized unit also includes custom designed noise reduction adhesive, pads, and strategically placed self-adhesive sound/vibration reduction material wall insulation to mitigate sound and vibration.

The units in general have the above features, but where the optics may optionally be provided in a two optic array of a-b options, where "A" is on, but "B" is on if A fails.

Fan assemblies are needed for portable home-sized hydroxyl generators, to pull air therein from the surrounding room and push it out into the room with purified hydroxyl filled air.

For safety, an air pressure safety switch is provided, so that when air flow is not detected, this unit will be dormant. A Micro Switch shuts down all systems should the device be opened when unit is in the ON/RUN position.

In a double optic option one optic may be on to create the hydroxyl radical and the existing fan directs the hydroxyls with the dual optic availability, should there be an abnormal intrusion of VOCs' or pathogens into the HVAC system, then the sensor would alert the hydroxyl device and the second optic would then come online in order to neutralize the threat load.

The hydroxyl generator includes a housing having an air inlet at one end and air outlet at an opposite end thereof, wherein the housing contains a plurality of spaced crystal-spliced UV optics, the UV optics being tubular, medical grade pure quartz optics designed to emit/irradiate ultraviolet in the nanometer wavelength/ultraviolet spectrum of between 100 and 400 nanometers for deactivating chemicals and pathogens in the breathable air for the respective flight deck and passenger compartments, on mass transit rail and road vehicles, in building ducts and other human occupied spaces. The air inlet at one end and the air outlet at an opposite end of the housing are provided for exposing ambient water vapor to the plurality of spaced crystal-spliced UV optics, to generate the hydroxyls. Preferably, the housing comprises a lengthwise extending hollow housing having a polygon shape in cross section, with adjoining lengthwise extending flat walls.

In summary the hydroxyl generator includes a housing having an air inlet at one end and air outlet at an opposite end thereof, wherein the housing contains a plurality of spaced crystal-spliced UV optics, the UV optics being tubular, medical grade pure quartz optics designed to emit/irradiate ultraviolet in the nanometer wavelength/ultraviolet spectrum of between 100 and 400 nanometers for deactivating chemicals and pathogens in the breathable air for the respective flight deck and passenger compartments, on mass transit rail and road vehicles, in building ducts and other human occupied spaces. The air inlet at one end and the air outlet at an opposite end of the housing are provided for exposing ambient water vapor to the plurality of spaced crystal-spliced UV optics, to generate the hydroxyls. Preferably, the housing comprises a lengthwise extending hollow housing having a polygon shape in cross section, with adjoining lengthwise extending flat walls.

BRIEF DESCRIPTION OF THE DRAWINGS

The present invention can best be understood in connection with the following drawings, which are not deemed to be limiting in scope.

FIG. 5A is a flow chart showing the electronic controls with respect to their position adjacent to the hydroxyl generator.

FIG. 6B further shows baffles at the air intake and air exit of the unit to promote an "S" shaped configuration of the airstream within the unit to prevent any undesirable and dangerous glare from direct exposure of persons in the room from the intense light rays of the quartz lamp optics.

DETAILED DESCRIPTION OF THE DRAWINGS

As used throughout this specification, the word "may" is used in a permissive sense (i.e., meaning having the potential to, or being optional), rather than a mandatory sense (i.e., meaning must), as more than one embodiment of the invention may be disclosed herein. Similarly, the words "include", "including", and "includes" mean including but not limited to.

The phrases "at least one", "one or more", and "and/or" may be open-ended expressions that are both conjunctive and disjunctive in operation. For example, each of the expressions "at least one of A, B and C", "one or more of A, B, and C", and "A, B, and/or C" herein means all of the following possible combinations: A alone; or B alone; or C alone; or A and B together; or A and C together; or B and C together; or A, B and C together.

Also, the disclosures of all patents, published patent applications, and non-patent literature cited within this document are incorporated herein in their entirety by reference. However, It is noted that the citing of any reference within this disclosure, i.e., any patents, published patent applications, and non-patent literature, is not an admission regarding a determination as to its availability as prior art with respect to the herein disclosed and claimed apparatus/method.

Furthermore, any reference made throughout this specification to "one embodiment" or "an embodiment" means that a particular feature or characteristic described in connection therewith is included in at least that one particular embodiment.

Thus, the appearances of the phrases "in one embodiment" or "in an embodiment" in various places throughout this specification are not necessarily all referring to the same embodiment. Therefore, the described features, advantages, and characteristics of any particular aspect of an embodiment disclosed herein may be combined in any suitable manner with any of the other embodiments disclosed herein.

Figures 1, 2:
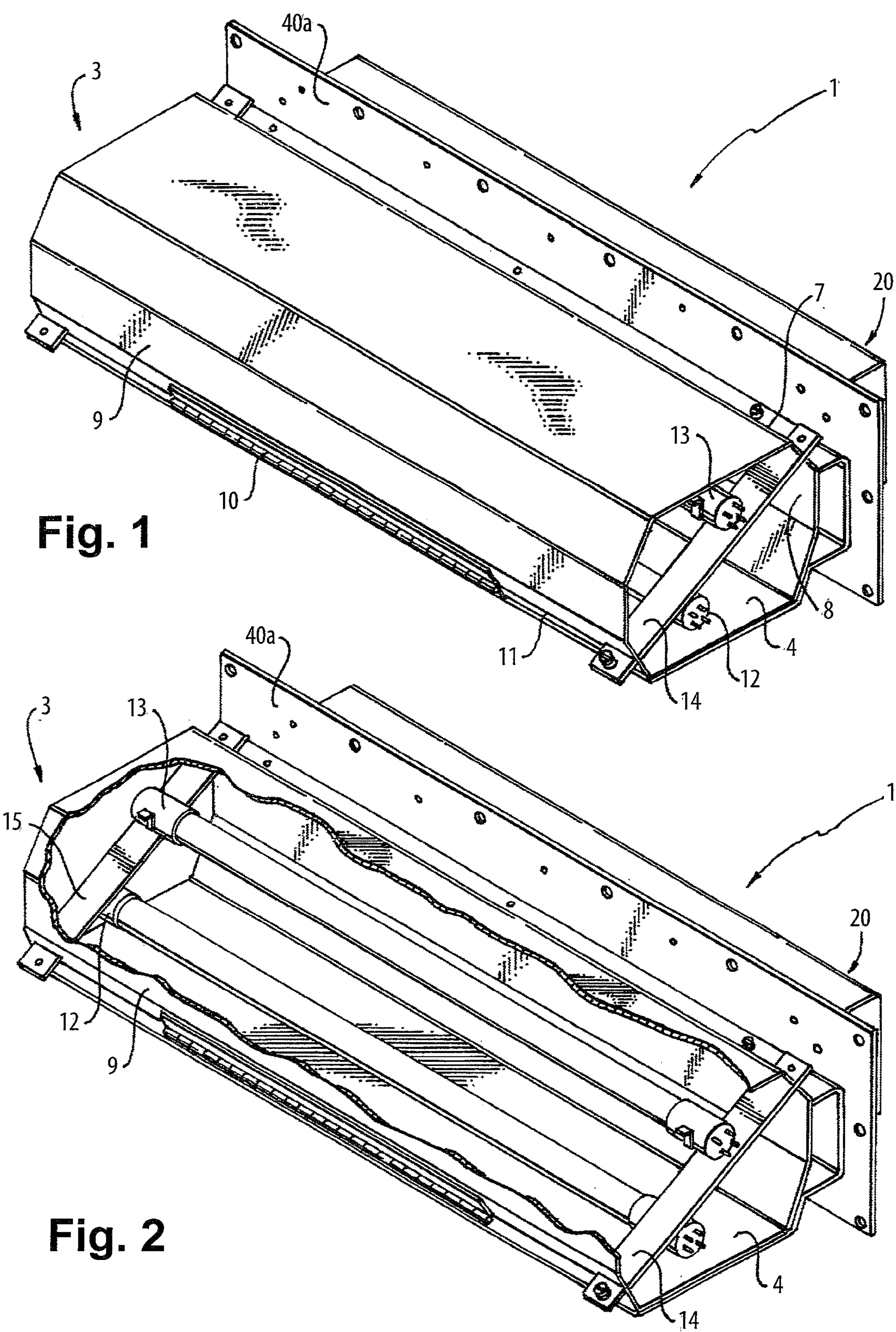
FIG. 1 is a perspective view of a polygonal hydroxyl generator shown in a closed position.
FIG. 2 is a perspective view of the hydroxyl generator of FIG. 1 shown in partial cross section with an open view of the interior of the hydroxyl generator.

FIG. 1 shows a hydroxyl generator 1, including a polygonal-shaped housing, including a bracket brace 14 for supporting crystal-spliced UV optics 12 and 13 within respective C-shaped spring clasps 12*a* and 13*a*, which are each respectively mounted on bracket brace 14, which are mounted parallel lengthwise to each other inside the clamshell hexagon housing, but staggered so that UV optic 12 is on a different side of the bracket 14 from the side on which UV optic 13 is located, wherein the crystal spliced UV optics 12 and 13, each have a length that runs substantially the entire length of the housing of the hydroxyl generator 1. A preferred example for the crystal-spliced UV optics 12 and 13 is the GPH457T5L/4P UV Optic 4-pin Base 18" GPH457T5 of Light Spectrum Enterprises of Southampton; these optics 12 and 13 are typically 18 inches long and are made of quartz. The tubular optics 12 and 13 are composed of pure Medical Grade quartz crystal in the portion of the optics which creates the hydroxyls. The present invention adds additional frequencies to the pure crystal optics. These tubular optics 12 and 13 generate 'Harmonic' bio-mimicry nonchemical process of the present invention which enables the production of desired atmospheric hydroxyls at a rate commensurate with the VOC/Bio loading in that particular space to be treated with the hydroxyls.

In contrast to the medical grade quartz tubular optics, it is noted that total glass tubes cannot be used when generating UV. The glass would simply be vaporized. Some companies use a fusion of glass and quartz crystal, which is not optimal as the glass portion creates a frequency that actually attracts contaminants. This problematic action neutralizes the desired UV action. Such a fusion lamp of glass and quartz crystal is cheaper to produce, however the poor performance of the lamp would be the end result.

Figure 3:
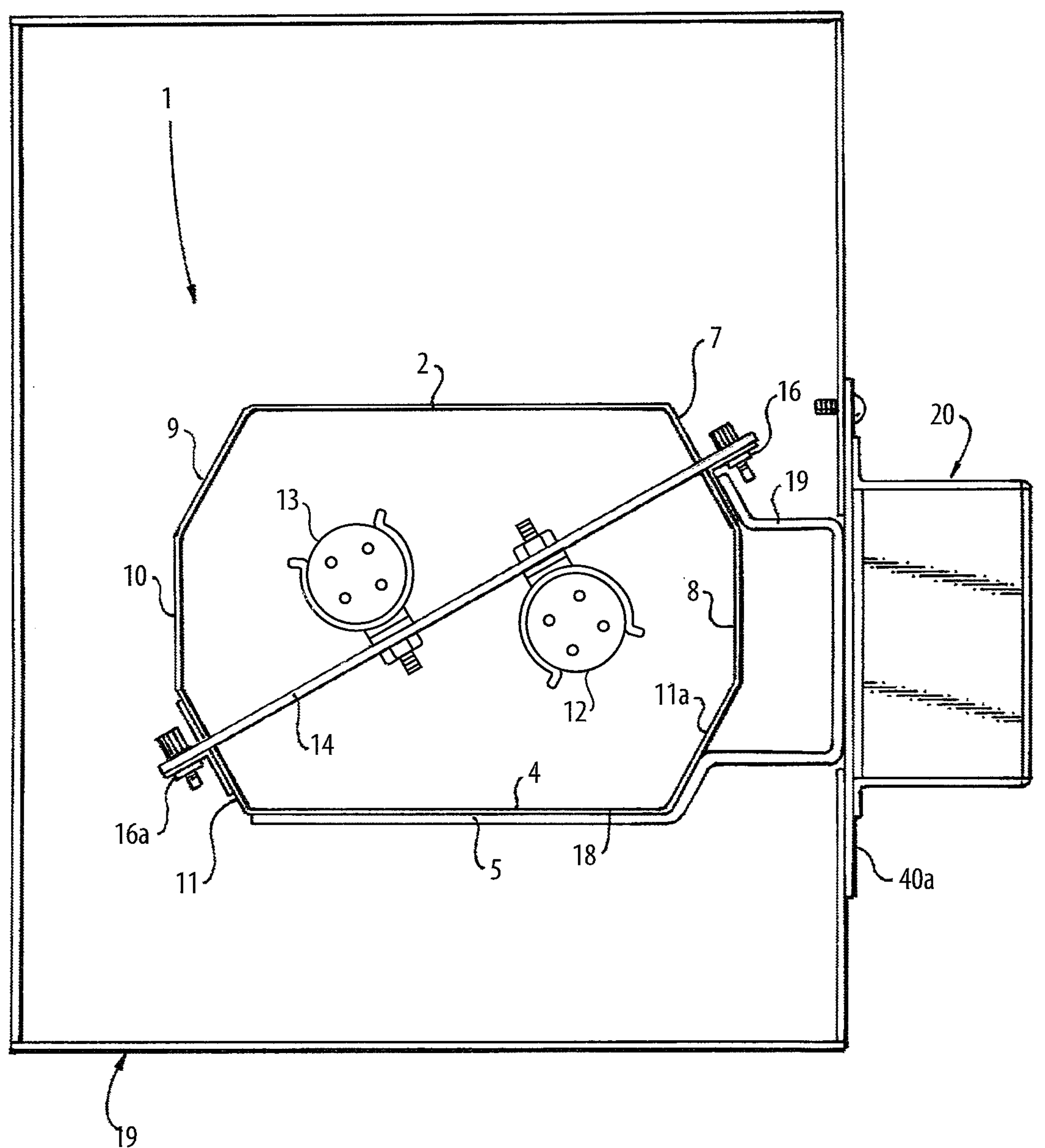
FIG. 3 is an end view in cross section of the hydroxyl generator of FIG. 1, with two UV optics for generating hydroxyl radicals.
Figure 4:
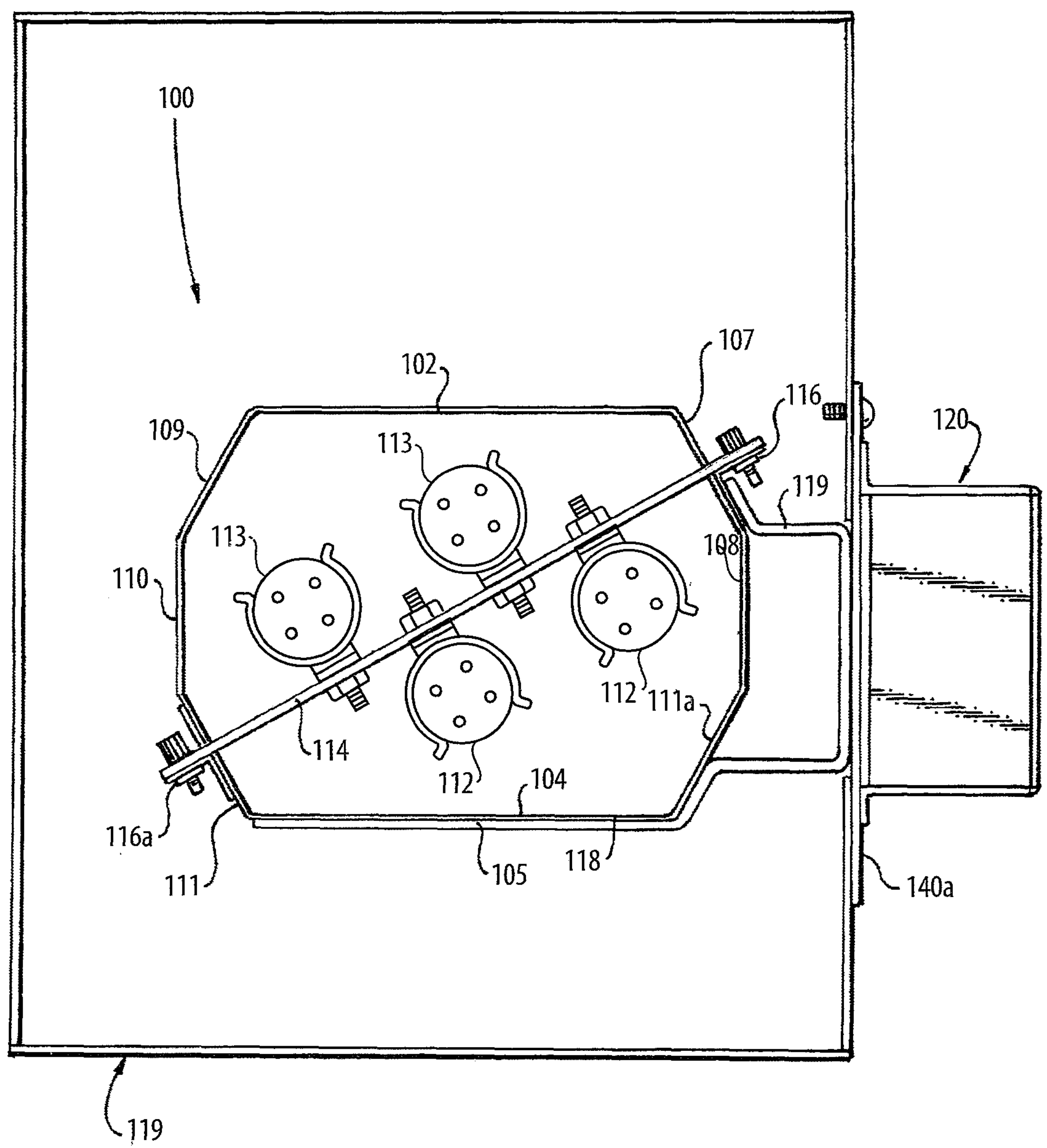
FIG. 4 is a cross sectional end view of an alternate embodiment for a hydroxyl generator, showing four UV hydroxyl generator optics within the polygonal hydroxyl generator.

Other similar Medical Grade quartz tubed UV optics can be used. The optics 12 and 13 are preferably symmetrically positioned in the housing of the hydroxyl generator 1, as shown in FIGS. 3 and 4 to operate most efficiently, but where in FIG. 3 the crystal spliced UV optics 12 and 13 are staggered so that UV optic 12 is on a different side of the bracket brace 14 from the side on which UV optic 13 is located. FIG. 4 shows an alternate embodiment where there are two pairs of UV optics, namely 112, 112 and 113, 113. The UV optics 112, 112 are staggered to the right on one bottom side of the horizontal bracket brace 114, but are separated by upright bracket brace 114. Likewise, UV optics 113 and 113 are respectively staggered to the left on the opposite top side of the horizontal bracket brace 114, also separated from each other by upright bracket brace 114. Optics pairs 112, 112 and 115, 113 are supported within pairs of respective C-shaped spring clasps which pairs of optics 112, 112 and 113, 113 are each respectively mounted on bracket brace 114, and which pairs of optics 112, 112 and 113, 113 are mounted parallel lengthwise to each other inside the clamshell hexagon housing 100 of FIG. 4.

The clamshell hexagon housing hydroxyl generator 1 has a clamshell configuration, including a clamshell top wall 2, upper side walls 7, 8, 9 and 10, fasteners 16*a*, 16*a*, a hinge 6 for opening the polygonal clamshell housing 1 and a bottom clamshell portion, including a bottom wall 4 and angle-oriented walls 11 and 11*a*, whereby the polygon housing opens hinge 6 to expose the inside of the hydroxyl generator 1 for maintenance and/or repair. In addition, the polygon hydroxyl generator enclosure can be removed from the air duct wall 40A for such maintenance and repair. The hydroxyl generator also includes an adjacent electronic control box 20, which is attachable to the clamshell housing of the hydroxyl generator 1. Alternatively, as shown in FIGS. 3 and 4, the electronic control box 20 is preferably located outside of the air path, which may be a duct or other conduit. It can alternatively be attached outside of the duct. It communicates with the UV optics wirelessly. The reason for the polygon shape is that the hydroxyl generators generated by the crystal-spliced UV optics 12 and 13 are scattered upon being generated by the optics 12 and 13, but they dissipate quickly if not activated by contact with reflective non-absorbent surfaces inside the respective walls of the polygon. The purpose of the polygon shape is that when the hydroxyl radicals are generated, they are emitted radially in all directions from the UV crystal-spliced optics 12 and 13 and normally would dissipate when scattered radially from the optics. In order to permit the hydroxyl radicals to maintain their desired electron charge and ability to contact and inactivate mold, volatile organic compounds, pathogens, bacteria, virus, etc., they need to reflect and refract off of the reflective non-absorbent walls continuously, within the reaction chamber confined space. As atmospheric hydroxyls are being activated by being created and excited in back-and-forth activity, the air inside the air duct/plenum 40*a* will contact the activated hydroxyl radicals with the end result of the neutralization of any impurities, such as VOCs, virus, bacteria, fungi, etc., in the air and surfaces.

Furthermore, once these radicals are emitted, they can penetrate any crevices in any area, such as in hydroponic greenhouse plant media growing vessels, such as between seats of aircraft, mass transit rail and road vehicles, in building ducts and wall surfaces and other human occupied spaces, such as individual rooms with small self-contained hydroxyl generators, between the surfaces of seats and shelving, and anywhere where ultraviolet light by itself would not be capable of eradicating the undesirable VOCs, fungi, virus, bacteria, etc. In the aircraft environment, the polygon-shaped housing is strategically located within an air supply unit in an airport terminal building, or it can be located within a remote cart not located near the aircraft, on the tarmac of the airport, and preferably it may be provided in the air systems separately of an aircraft cabin, including the flight deck and the areas of the main cabin where passengers are seated. Therefore, the polygon shaped housings may also be strategically located in mass transit rail and road vehicles, in building ducts, in individual rooms, and wall surfaces and other human occupied spaces As shown in the end view of FIG. 3, the inside of the polygon housing 1 is located below the field of vision within the sealed off plenum so that the ultraviolet (UV) crystal-spliced tubular optics 12 and 13 will not be exposed to the eyes of any observers. Therefore, while the hydroxyl radicals are being generated, the UV energy which create hydroxyl generation from optics 12 and 13 are completely sealed off so that when the optics 12 and 13 are operational, the UV light emanating therefrom will not penetrate outside of the polygonal housing. Baffles, optionally located outside of the hydroxyl generators, but in the vicinity of the hydroxyl generators, prevent the UV light from exposure to persons. Additionally, fibrous filters may be provided at input and outlet areas of the housing containing the hydroxyl generator portion with the UV optics, to capture any undesirable airborne particulates, such as dirt and dust and other particles which may compromise the sensitive quartz material of the UV optics. There is no restriction regarding the active flow of the hydroxyls inside the hydroxyl generator 1 and no interference with the excitement of the hydroxyls produced by the exposure of ambient water vapor within the polygon shaped housing with the UV optics 12 and 13 irradiating light that causes the —OH radicals to form.

FIG. 4 shows an alternate embodiment for a four optic version, where polygon hydroxyl generator enclosure 100, having top wall 102, side walls 107, 108, 109, 110 of an upper shell, as well as lower walls 105, 111*a*, 111*b* of the clamshell housing. The clamshell housing has inner walls 104 against which the hydroxyls being formed contact repeatedly during formation. FIG. 4 also shows the electronics control box 120, attached to the clamshell housing by brackets 119. The respective pairs of optics 112, 112, and 113, 113 are supported within respective pairs of C-shaped spring clasps, which are each respectively mounted on bracket brace 114, which are mounted parallel lengthwise to each other inside the clamshell hexagon housing 100. The upper half of the clamshell housing is connected to the lower half of the clamshell housing by fasteners 116, 116*a*. Clamshell housing 100 is openable via a hinge located near fastener 116*a*.

Figure 5:
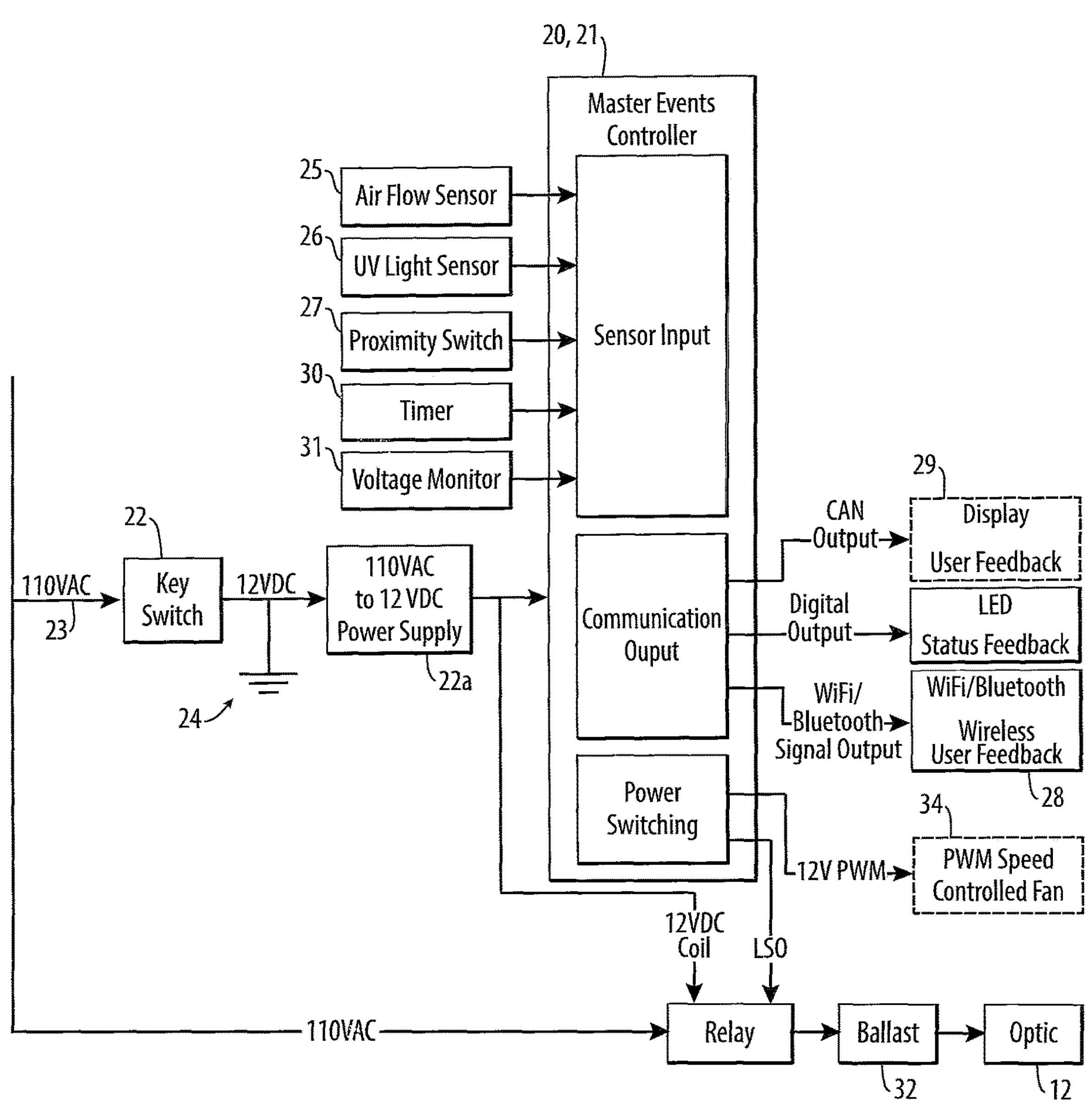
FIG. 5 is a block diagram of the electronic controls of the hydroxyl generator of FIGS. 1-3 and 4.

FIG. 5 is a block diagram showing the network and electronics of the control box 20. Initially AC power 23 of 110 VAC is converted by converter 22 to low voltage 12 VDC, or else a low voltage battery alternatively delivers 12 VDC to a secure Key Switch 22*a*, to provide power to the Master Events Controller 20, which may have a microprocessor 21. The Master Events Controller 20 also receives input from sensors, such as Air Flow Sensor 25, UV Light Sensor 26, Proximity Switch 27 (detecting opening of the enclosure), Timer 30 and Voltage Monitor Sensor 31. These sensors provide Sensor Input to the Master Events Controller 20. Power Switching in the Master Events Controller 20 sends 12V Pulse Width Modulation data to a PWM Speed Controlled Fan 34, to send air through the hydroxyl generator unit 1 or 101, or to stop the flow of air when needed for safety and maintenance situations. The Power Switching also sends data via a Large Serve Outlet (LSO) to a Relay, which controls the Ballast 32, providing power to the Crystal UV Optics 12, which creates the needed hydroxyls within the hydroxyl generators 1 or 101. The Master Events Controller 20 also has a Communications Output, which can send data via a Controller Area Network (CAN) to a Visual Display 29 for user feedback. The Communications Output of the Master Events Controller 20 also sends digital data wirelessly as output to Status Feedback Units. The Communications Output of the Master Events Controller 20 also sends Wi-Fi/Bluetooth® Signal output to Wireless input devices 28 for Wireless user feedback during use.

FIG. 5A is a diagrammatic flow chart, showing the electronic control box 20 of FIGS. 1, 2 and 3, which is also equivalent to the electronic control box 120 of FIG. 4. Adjacent to the hydroxyl generator 1 or 101, which in FIGS. 1-3, the hydroxyl generators are attached by one or more brackets 19 to the electronic control box 20. Similarly, the electronic control box 120 is attached by brackets 119 of FIG. 4.

In the diagrammatic flow chart of FIG. 5A, related to the electrical block diagram of FIG. 5, the control box 20 includes a microprocessor 21 for controlling the sensors and switches, which control the operation of the optics 12 and 13, or 112 and 113, of the hydroxyl generators 1 shown in FIGS. 1-3 and 4 respectively. There is also a power source being either a DC low-voltage battery 24, or an AC plug 23, to provide higher-voltage AC power. When the AC is used, a converter 22 can be provided to convert high-voltage AC to low-voltage DC power for operating any of the sensors and control elements within box 20. Box 25 of FIG. 5A discloses the detector 25 to detect whether airflow is on, so that the optics 12 and 13 will only be on after airflow is confirmed, so that they are not on when there is no airflow. Box 26 of the diagrammatic flow chart of FIG. 5A discloses the sensor 26 for detecting emitted light, and providing feedback to replace optics, including a secondary backup optic, which is also disclosed in box 26 of the flowchart of FIG. 5A. Box 27 of the diagrammatic flow chart of FIG. 5A discloses a detector with a proximity switch 27 detecting opening of the enclosure, and thereafter used to turn off the optics 12 and 13, to protect people from being exposed to the possible harmful UV light emitted from the optics 12 and 13. This detector with the proximity switch 27 shown in box 27 of the diagrammatic flow chart of FIG. 5A also includes a limit switch, a micro switch and sensors. Box 28 of the diagrammatic flow chart of FIG. 5A discloses the mobile phone application connection 28 for user feedback by wireless communication, such as Wi-Fi or Bluetooth® communications, between the operator, the control box 20 and hydroxyl generator 1 itself, together with a timer. The control box 20 also includes the LCD user feedback system 29, with a timer shown in box 29 of the diagrammatic flow chart of FIG. 5A with a timer, as well as a further timer 30 shown in box 30 of the diagrammatic flow chart of FIG. 5A, to provide feedback for regular maintenance. The voltage and frequency of AC main supply sensor 31 is shown in box 31 of the diagrammatic flow chart of FIG. 5A, Box 32 of the diagrammatic flow chart of FIG. 5A shows the voltage and frequency of the monitor of the ballast power outfit 32. Box 33 of the diagrammatic flow chart of FIG. 5A discloses a fire sensor 33, which detects excess heat in the system. Box 34 of the diagrammatic flow chart of FIG. 5A discloses a real time clock 34 which controls any fans providing and activating the airflow through the polygon hydroxyl generators 1.

Figure 5B:
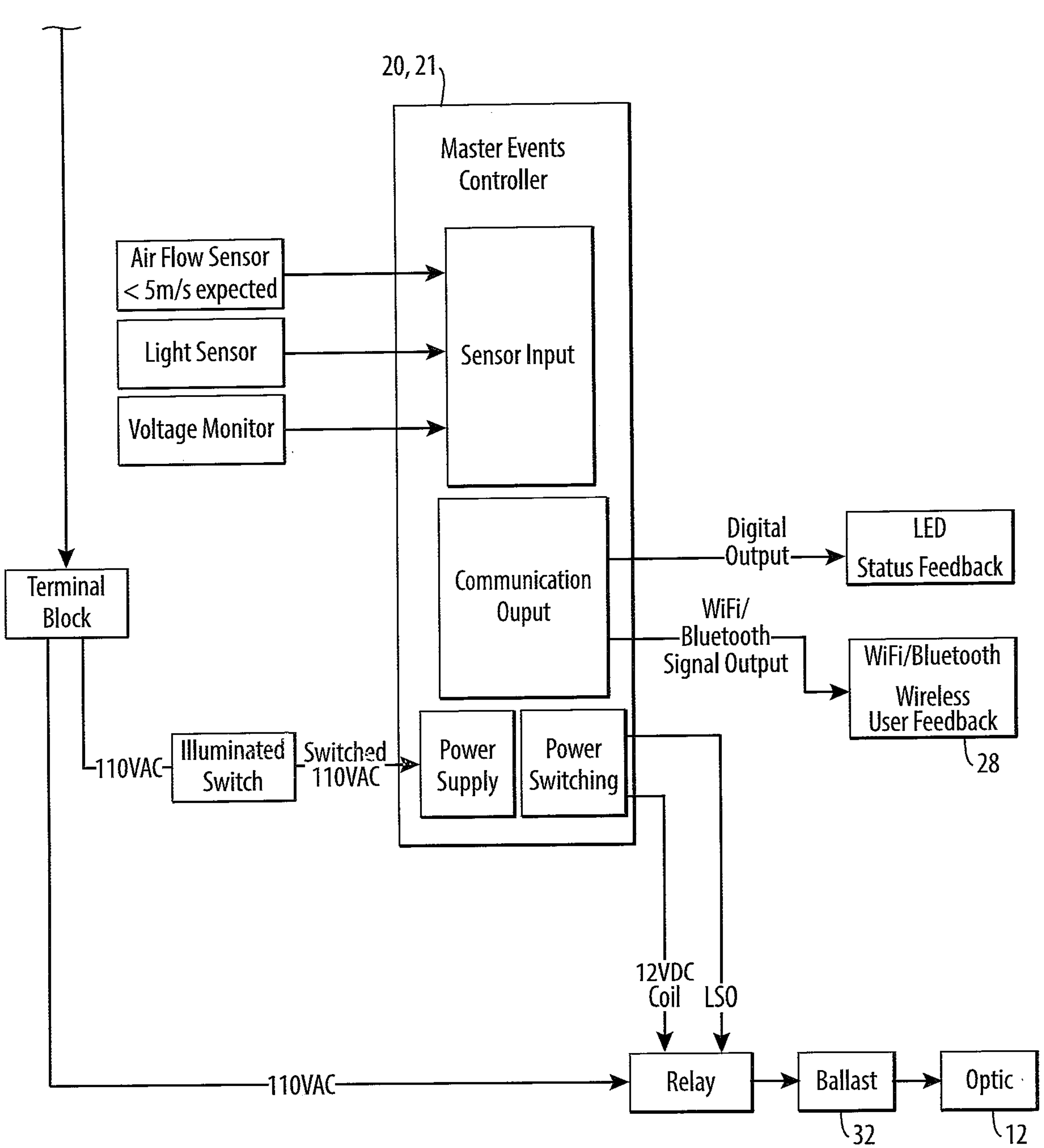
FIG. 5B is a block diagram of the electronic controls of the hydroxyl generator used in hydroponic greenhouse applications shown in FIGS. 6 and 6A, or in other applications requiring the electronic controls of FIG. 5B.
Figure 5C:
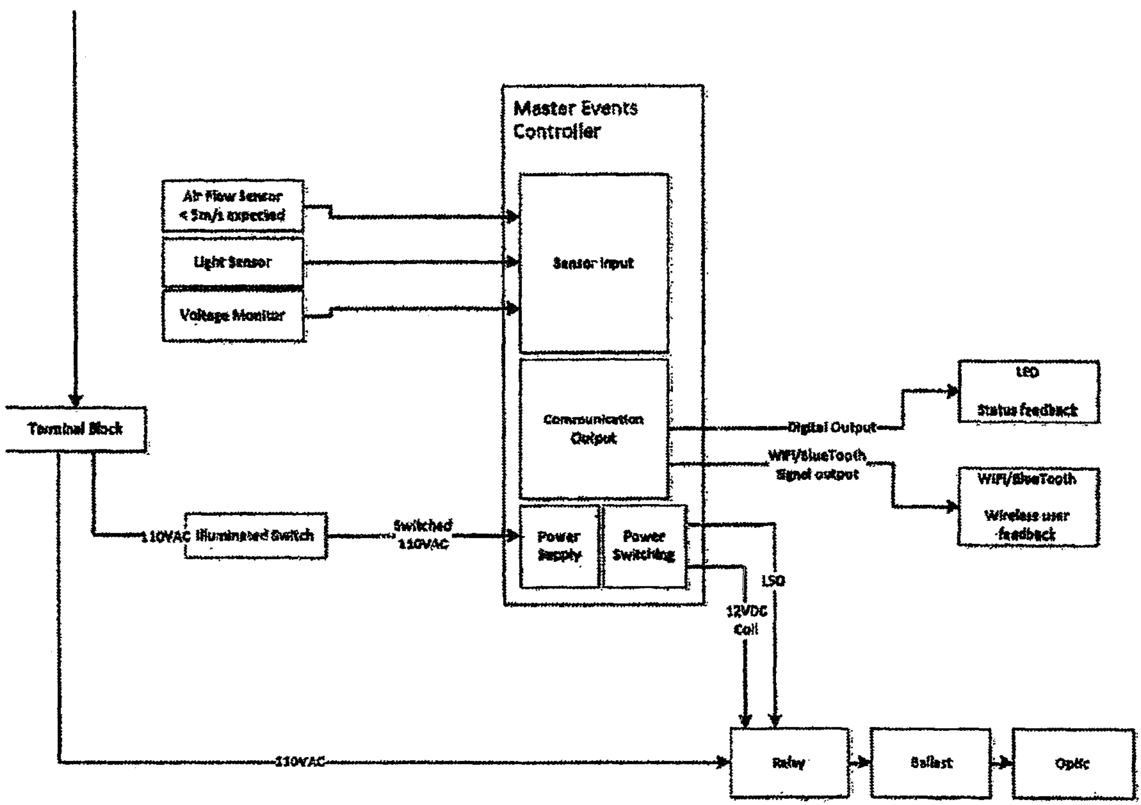
FIG. 5C is a block diagram of the electronic controls of the hydroxyl generator used in HVAC building duct applications, or in other applications requiring the electronic controls of FIG. 5C.

In the alternate embodiment shown in block diagram FIG. 5B, there are disclosed therein shown the following differences of block diagram FIG. 5B from block diagram FIG. 5, wherein in block diagram FIG. 5B the following features are shown:

1. The key switch (22*a*) can alternatively be positioned before the power supply (22);
2. The key switch (22*a*) can alternatively be a pushbutton;
3. The power supply (22) can alternatively be included in the Master Events Controller (MEC) 20;
4. The user feedback display (29) of FIG. 5 is not needed in FIG. 5B, because the Wi-Fi/Bluetooth® communication works with a mobile application;
5. The PWM Speed controlled fan (34) of FIG. 5 is not needed, because the hydroxyl generator 1 will be located in an existing duct with moving air; and,
6. The power to the relay (not numbered) in FIG. 5 can alternatively be provided by the Master Events Controller (MEC) 20 in FIG. 5B.

Example

Portable Room-Sized Generator Embodiment

Figures 6, 6A:
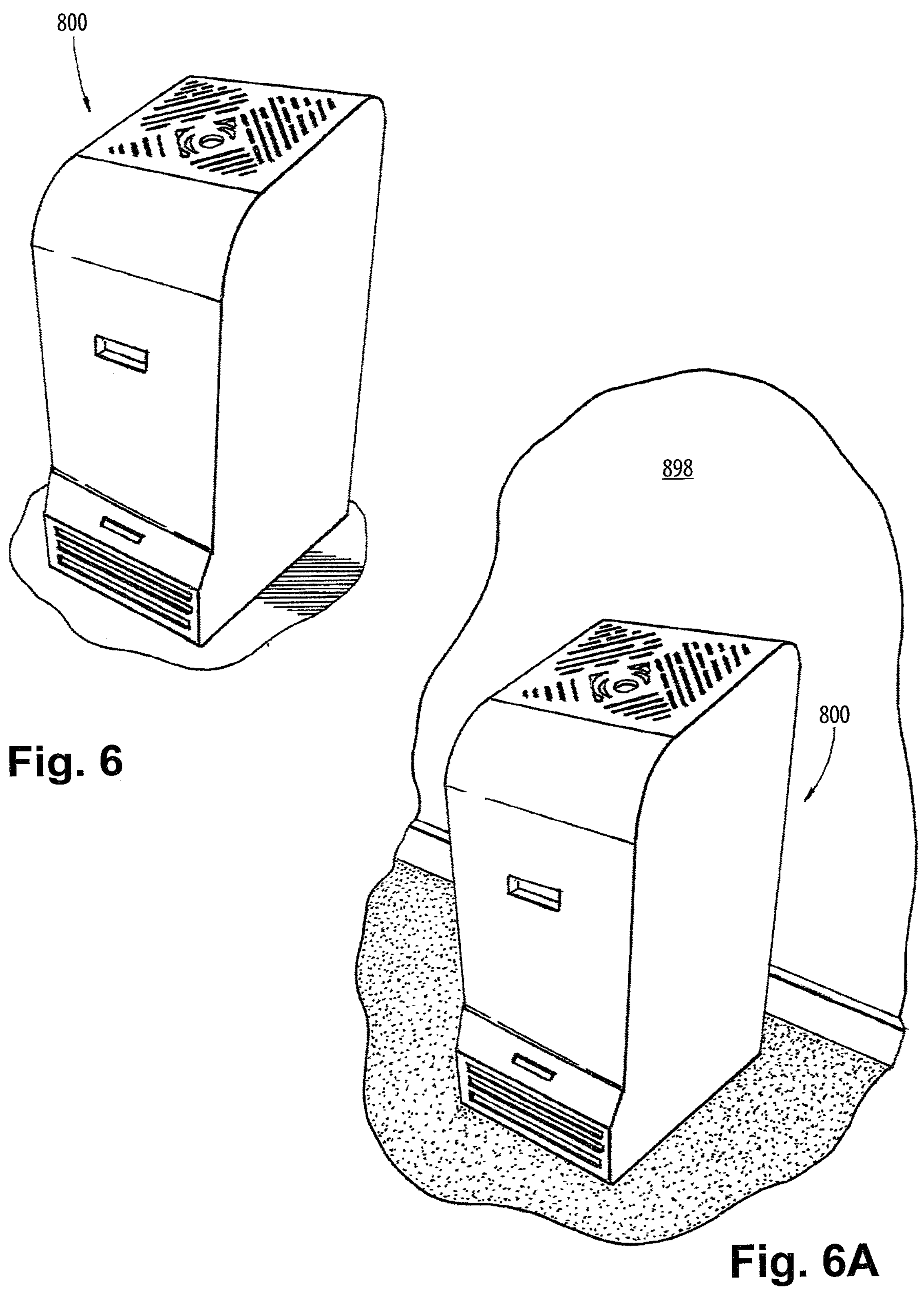
FIG. 6 is a perspective environmental view of a portable room size hydroxyl generator located on the floor in a room with office or residential furniture.
FIG. 6A is a perspective view of the portable room size hydroxyl generator mountable upon a wall of a room.
Figures 6B, 7:
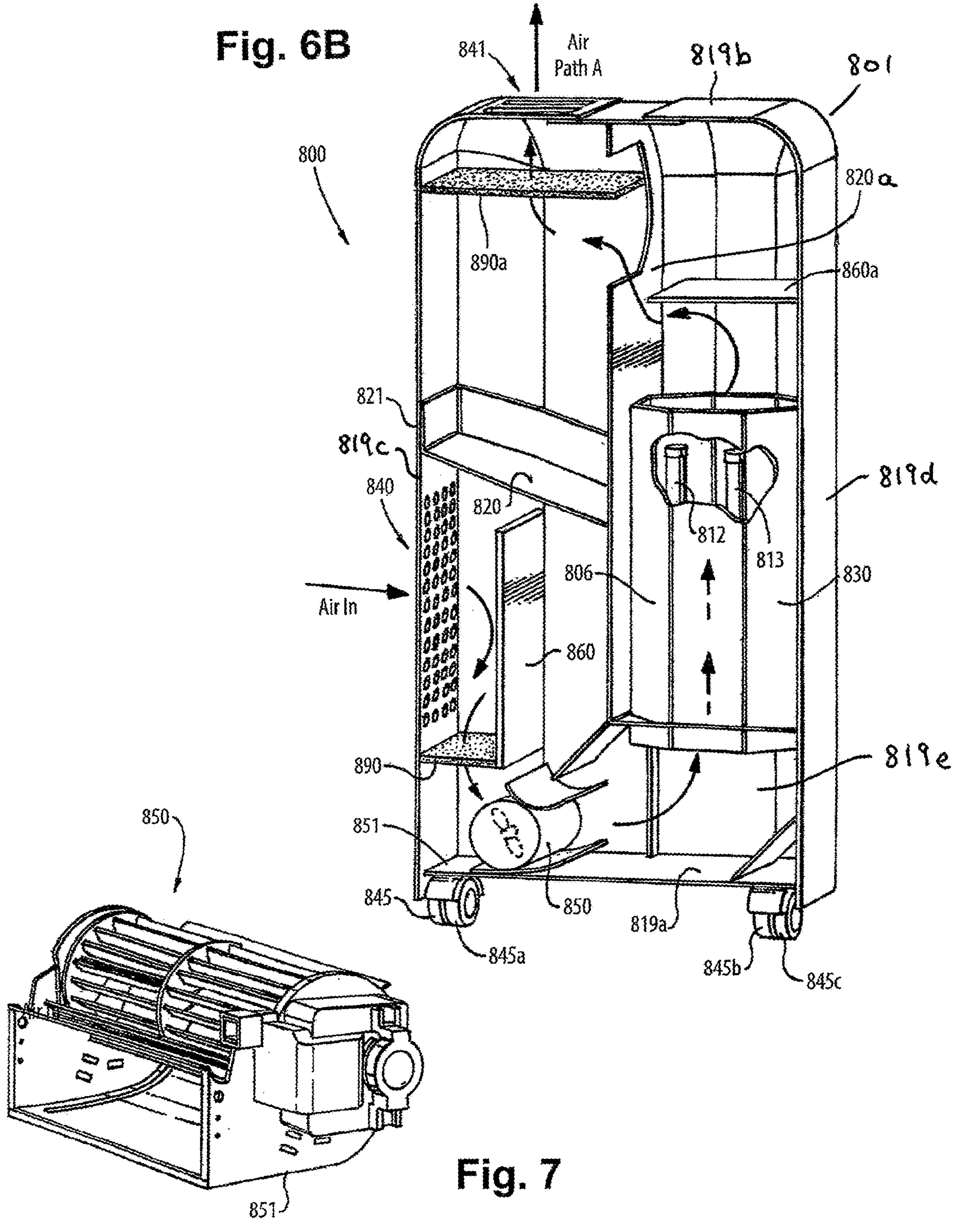
FIG. 6B is a cross sectional perspective view of an alternate embodiment for a portable room size hydroxyl generator, showing interior components, including an air intake grate, a directional fan for pulling the intake air and sending it in an air flow in the direction of the arrows indicated through a vertically oriented clamshell hydroxyl generator housing, having optics therein as well as interior walls to facilitate the exiting of purified air out of the portable room size hydroxyl generator to the occupied room in which the generator is located, as well as showing filters at the air intake and air exit of the airstream to capture any dirt or undesirable particles, which could compromise the quartz lamp optics.
FIG. 7 is a closeup perspective view of the airflow blower fan unit of the portable room size hydroxyl generator of FIGS. 6, 6A and 6B.
Figure 7A:
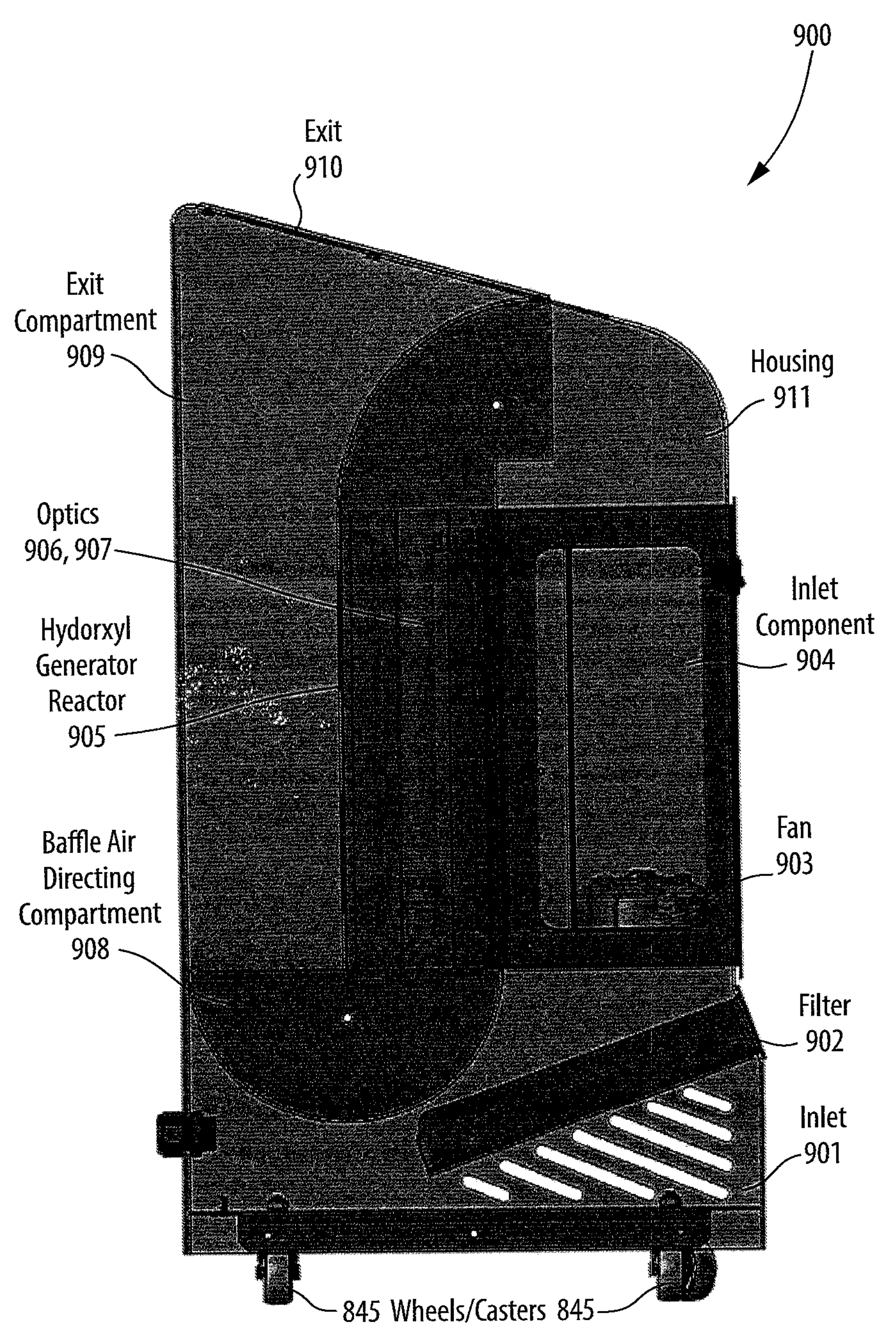
FIG. 7A is a side view in cross section of a preferred embodiment for a portable room-sized hydroxyl generator having a housing with "S-shaped" conducts to promote an "S-shaped" flow of the air within the hydroxyl generator The housing includes an air inlet and a filter to keep out dirt, dust and other contaminating particulates from entering and contaminating the optics within the centrally located hydroxyl generating reactor after which the air infused with hydroxyl radicals produced by contact or water vapor in the inlet air exposed to the UV light of the optics. A curved baffle type air directing conduit moves the air in the S-shaped curvature through an exit compartment and exit grille to the room in which the portable room-sized hydroxyl generator stands upon casters or wheels or is alternatively mountable upon a wall (not shown) in the room being serviced by the portable room-sized hydroxyl generator unit.
Figure 7B:
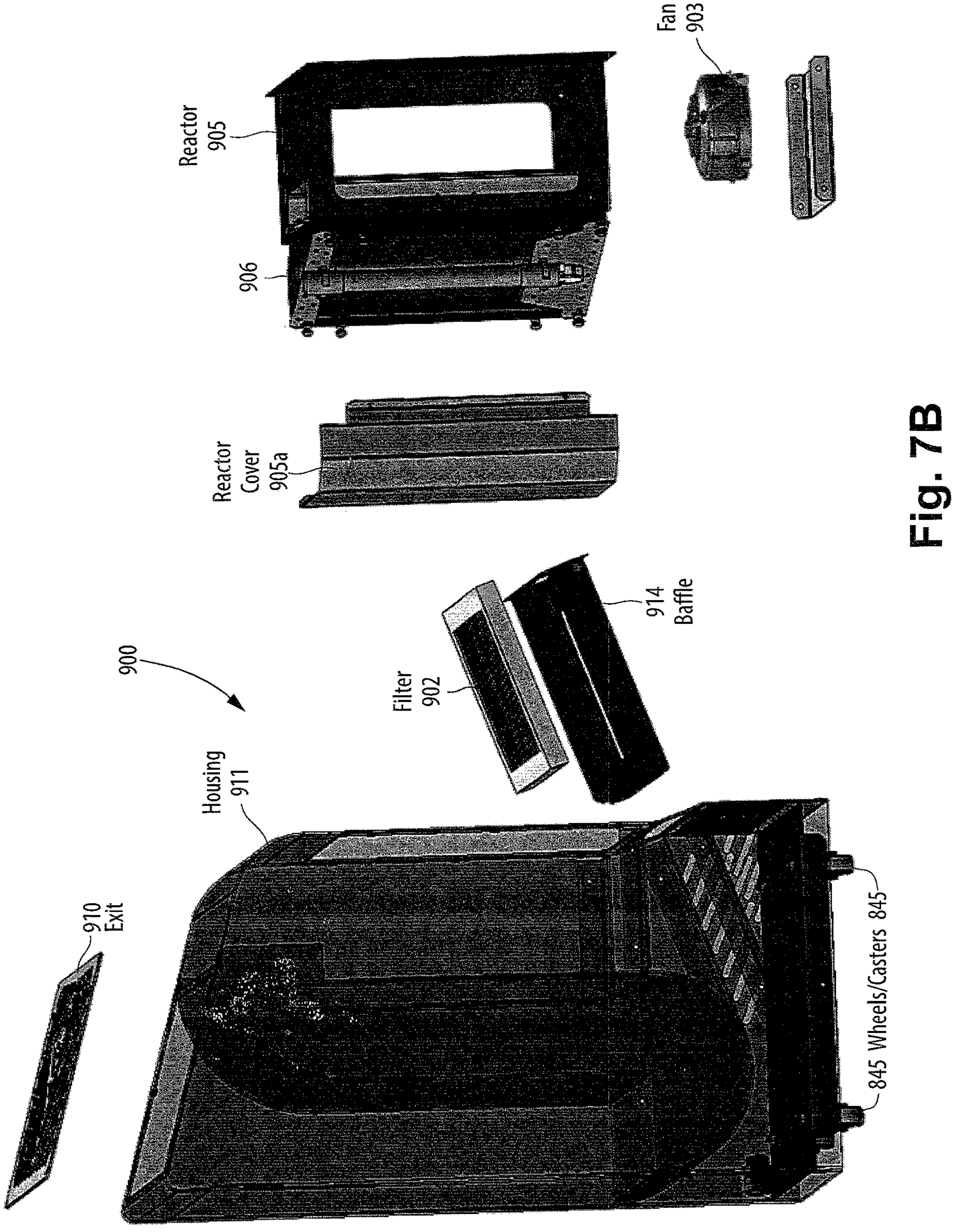
FIG. 7B is an exploded view of the portable room-sized hydroxyl generator as in FIG. 7A, showing the housing of hydroxyl generator, with caster wheels, and a filter and baffle conduct inside the air inlet of the housing. The hydroxyl generator reactor is also shown with an optic, fan and exit grille.

FIGS. 6-7B show polygon hydroxyl generators 800, which are removably positioned for lower power needs in smaller confined areas, such as individual rooms in a building or schoolhouse or nursing home. FIG. 6 shows a portable room sized unit 800 which can be provided, which will have a smaller interior volume for producing the optimal number of hydroxyls generated to purify the air/surfaces and crevices/creases within the aforesaid areas. Such a portable hydroxyl generator 800 includes a generator chamber housing 801, which is mounted on a bottom wall, 819*a* including casters or wheels 845, 845*a*, 845*b* and 845*c* on the bottom for moving the hydroxyl generator 800 around in a confined space area, such as an individual room.

Figure 5D:
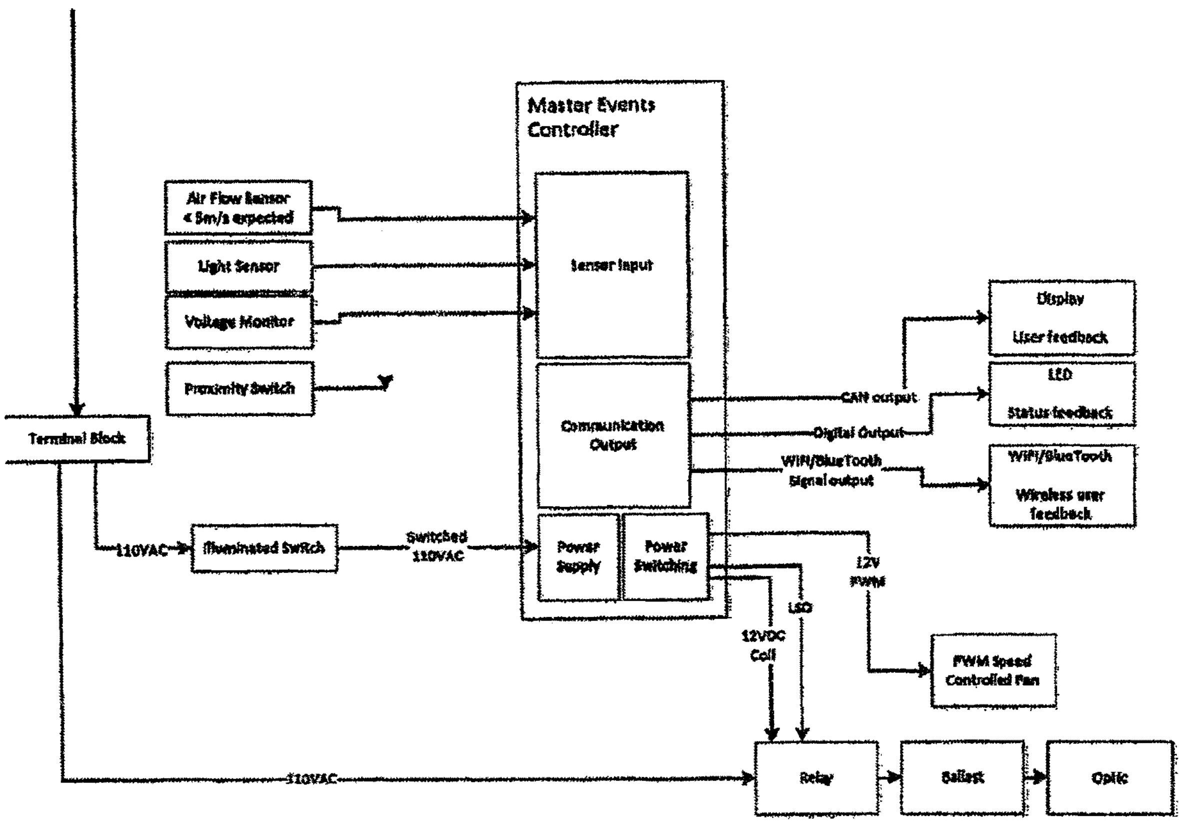
FIG. 5D is a block diagram of the electronic controls of the hydroxyl generator used in Portable Room-Sized Unit applications, or in other applications requiring the electronic controls of FIG. 5D, which include a proximity detector for safety reasons and a fan, such as a pulse width modulated fan, which regulates the air speed of the fan by regulating the voltage of the fan between on and off, to move air flow with air purifying generated hydroxyl radicals therethrough.

FIG. 5D is a block diagram of the electronic controls of the hydroxyl generator used in Portable Room-Sized Unit applications, or in other applications requiring the electronic controls of FIG. 5D, which include a proximity detector for safety reasons and a fan, such as a pulse width modulated fan, which regulates the air speed of the fan by regulating the voltage of the fan between on and off, to move air flow with air purifying generated hydroxyl radicals therethrough.

Alternatively, the unit 800 can be devoid of movable wheels or casters (not shown), but can be mounted upon a wall 898 (FIG. 6A).

Shown in FIG. 6B, the movable generator 800 also includes the housing polygon generator chamber housing 801, which houses therein a clamshell housing having a polygonal chamber 830, which has inside the UV light emitting optics 812, 813. Baffles 820 and 860 and 860*a* are located inside of the portable housing 801, but outside of clamshell housing chamber 830 with optics 812, 813 to limit any leaking of UV light from the crystal-spliced tubular optics 812, 813, which upon being engaged will generate the hydroxyl radicals flowing nearby. The unit 800 also includes an air intake 840 and air exit 841, as well as a partition 820*a* and space for the electronics, an air blower 850 which blows and pressurizes air to the chamber of the hydroxyl generator 830. Front bezel 821 is provided for controls and the air intake 840 is provided on one of the walls 819*c* of the aluminum unit 801, enclosing the housing generator 830 housing optics 812, 813 therein. The aluminum housing 801, or other suitable material, has side walls 819*c*, 819*d*, top wall 819*b* and bottom wall 819*a*, as well as rear wall 819*e* and front cover (not shown). When the aluminum cover is removed, it provides easy access for optic cleaning and/or replacement of the enclosed, sealed clamshell hydroxyl generator 830, which can be taken out and opened along its clamshell hinge 806. The air is passed through the intake, blown by the blower 850, then through the polygonal generator chamber housing 830 and out through an air outlet 841. The blower 850 is mounted by a mount 851 within the housing 801.

FIG. 6B also shows a side perspective view in cross-section of the hydroxyl generator 800 for residential home use, showing the "S-curve" diversion of the incoming and outgoing airflow "A", which diversion is achieved by light blocking baffles 860 and 860*a*, where one or more staggered baffles 860*a* are at the air flow exit portion 840 of the hydroxyl generator housing 801 for residential rooms, and also with one or more staggered baffles 860 are at the air flow entry point 840 of the hydroxyl generator housing 801. The staggered baffles 860 and 860*a* are configured to block inadvertent eye damaging light emanating from the optics within the polygonal optics bearing clamshell hydroxyl generator housing 830, especially for curious short children or leased service dogs for people in need of canine assistance while visiting in a residential building room, who might tend to stare and look at the hydroxyl generator 800, located on the floor of the room.

FIG. 6B also shows dirt and particulate-capturing filters 890, 890*a* at the air intake 840 and air exit 841 of the airstream to capture any dirt or undesirable particles in the air, whether part of the air stream or adjacent air surrounding the portable room sized hydroxyl generator 800, which could compromise the quartz lamp optics 812, 813.

FIG. 7 shows one example of an airflow blower fan unit of the portable room size hydroxyl generator of FIGS. 6, 6A and 6B. However, any shape or configuration for an air moving fan structure can be employed.

For example, a preferred embodiment for a portable room sized hydroxyl generator is shown in drawing FIGS. 7A and 7B.

FIG. 7A is a side view in cross section of a preferred embodiment for a portable room-sized hydroxyl generator 900 having a housing 911 with "S-shaped" conducts to promote an "S-shaped" flow of the air within the hydroxyl generator 900 The housing 911 includes an air inlet 901 and a filter 902 to keep out dirt, dust and other contaminating particulates from entering and contaminating the optics 906, 907 within the centrally located hydroxyl generating reactor 905 after which the air infused with hydroxyl radicals produced by contact or water vapor in the inlet air exposed to the UV light of the optics 906, 907. A curved baffle type air directing conduit 908 moves the air in the S-shaped curvature through an exit compartment 909 and exit grille 910 to the room in which the portable room-sized hydroxyl generator 900 stands upon casters or wheels 912, 913 or is alternatively mounting upon a wall in the room being serviced by the portable room-sized hydroxyl generator unit 900.

FIG. 7B is an exploded view of the portable room-sized hydroxyl generator 900 as in FIG. 7A, showing the housing 911 of hydroxyl generator 900, with caster wheels 912, 913 and a filter 902 and baffle conduct 914 inside the air inlet of the housing 911. The hydroxyl generator reactor 905 is also shown with a cover 905*a* removed, an optic 906, fan 903 an exit grille 910.

CONCLUSION

The hydroxyl generator systems of the present invention are designed to neutralize and destroy virus' everywhere safely and effectively, while purifying and sanitizing breathable heated, ambient, or cooled air emanating from a source and neutralizing up to 99.9999% of tested virus, including Covid-19 virus. The present invention also helps occupants an occupied space who are afflicted with asthma and airborne allergies, including full air and surface protection, including in crevices between other surfaces.

The hydroxyl generator systems of the present invention can be placed in any environment where pristine air is required, in a state of the art technology that is chemical free, safe for people, pets and plants.

In the foregoing description, certain terms and visual depictions are used to illustrate the preferred embodiment. However, no unnecessary limitations are to be construed by the terms used or illustrations depicted, beyond what is shown in the prior art, since the terms and illustrations are exemplary only, and are not meant to limit the scope of the present invention.

It is further known that other modifications may be made to the present invention, without departing the scope of the invention, as noted in the appended Claims.

What is claimed:

1. A portable air purification system (800) configured to clean air in a room of a residence, said air purification system comprising:

a hollow housing (801), said hollow housing comprising:

an air inlet (840) on a lower portion of a first side wall (819*c*) of said hollow housing;

an air outlet (841) in a top wall (819*b*) of said hollow housing;

a partition wall (820*a*), said partition wall configured to extend downwardly from said top wall (819*b*);

wherein said partition wall (820*a*) is configured to form a first vertical chamber bounded by said first side wall (819*c*) and said partition wall (820*a*), and a second vertical chamber bounded by said partition wall (820*a*) and a second side wall (819*d*);

a baffle (820), said baffle (820) configured to extend from said first side wall (819*c*) to said partition wall (820*a*) to separate said first vertical chamber into an upper chamber and a lower chamber;

wherein said baffle (820) is configured to inhibit fluid communication between said upper chamber and said lower chamber;

wherein said air inlet (840) is configured to admit room air into said lower chamber;

wherein said partition wall (820*a*) is configured to extend down from said top wall (819*b*) only partway to a bottom wall (819*a*) of said hollow housing to thereby provide an interconnection between said lower chamber and said second vertical chamber;

an air blower (850), said air blower positioned in said lower chamber of said hollow housing (801) between said air inlet (840) and said interconnection between said lower chamber and said second vertical chamber;

wherein said air blower is configured to create a pressurized air flow through said interconnection and into at least said second vertical chamber;

a particulate filter (890), said particulate filter positioned between said air inlet (840) and an intake of said air blower (850), said particulate filter (890) thereby configured to filter room air before entering said air blower;

a hydroxyl generator (830), said hydroxyl generator positioned in said second vertical chamber and comprising:

a linearly elongated housing configured to extend parallel to an axial direction of said second vertical chamber, and to extend from a first end to a second end, with an opening to form an air inlet at said first end and an air outlet opening at said second end, to receive the pressurized air flow in said second vertical chamber through said linearly elongated housing;

at least one UV bulb (812) configured to emit ultraviolet light to generate hydroxyl radicals from water vapor contained within the pressurized air flow; and means for supporting said at least one UV bulb (812) within said linearly elongated housing, and for orienting said at least one UV bulb parallel to a direction of the pressurized air flow in said linearly elongated housing; and an opening in said partition wall (820*a*) formed in proximity to said top wall (819*b*), to thereby interconnect an upper portion of said second vertical chamber with said upper chamber, and permit the pressurized air that exits said hydroxyl generator to flow into said upper chamber and out of said air outlet (841).

2. The portable air purification system (800) according to claim 1, wherein said baffle (820), said partition wall (820*a*), said interconnection between said lower chamber and said second vertical chamber, said second vertical chamber, and said upper chamber form a flow path configured to create an S-shaped flow of the air within said hollow housing (801).

3. The portable air purification system (800) according to claim 2, wherein said linearly elongated housing is formed to have an octagonal cross-sectional shape.

4. The portable air purification system (800) according to claim 3, further comprising: a baffle (860*a*) configured to extend from said second side wall (819*d*) partway to said partition wall (820*a*), to thereby block the UV light exiting said second end of said linearly elongated housing from reaching said air outlet (841).

5. The portable air purification system (800) according to claim 4, further comprising: a plurality of casters secured to said bottom wall (819*a*) to permit rolling movement of said portable air purification system within the residence.

6. The portable air purification system (800) according to claim 4, wherein said hollow housing (801) is configured to mount to a wall of the room.

7. The portable air purification system (800) according to claim 4, further comprising: a removable cover configured to provide access to said linearly elongated housing to permit replacement of each said at least one UV bulb.

* * * * *